(12) United States Patent
Bellqvist et al.

(10) Patent No.: US 7,051,758 B2
(45) Date of Patent: May 30, 2006

(54) SCALABLE INLET LIQUID DISTRIBUTION SYSTEM FOR LARGE SCALE CHROMATOGRAPHY COLUMNS

(75) Inventors: Peter Bellqvist, Uppsala (SE); Klaus Gebauer, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 336 days.

(21) Appl. No.: 10/476,903

(22) PCT Filed: May 10, 2002

(86) PCT No.: PCT/EP02/05144

§ 371 (c)(1),
(2), (4) Date: Nov. 4, 2003

(87) PCT Pub. No.: WO02/093159

PCT Pub. Date: Nov. 21, 2002

(65) Prior Publication Data

US 2004/0140007 A1   Jul. 22, 2004

(30) Foreign Application Priority Data

May 11, 2001 (GB) .............................. 0111486.7

(51) Int. Cl.
*B15D 15/08* (2006.01)
(52) U.S. Cl. .............................. 137/561 A; 210/198.2; 251/366
(58) Field of Classification Search ............ 137/561 A; 210/198.2, 656; 239/565; 251/366

See application file for complete search history.

(56) References Cited

U.S. PATENT DOCUMENTS

| | | | |
|---|---|---|---|
| 3,640,822 A * | 2/1972 | Hrdina | 210/635 |
| 4,537,217 A | 8/1985 | Allen, Jr. | |
| 4,582,608 A * | 4/1986 | Ritacco | 210/656 |
| 4,743,373 A * | 5/1988 | Rai et al. | 210/198.3 |
| 4,891,133 A | 1/1990 | Colvin, Jr. | |
| 5,141,635 A | 8/1992 | LePlang et al. | |
| 5,354,460 A | 10/1994 | Kearney et al. | |
| 5,423,982 A | 6/1995 | Jungbauer et al. | |
| 6,289,914 B1 * | 9/2001 | Tommasi | 137/15.18 |

* cited by examiner

*Primary Examiner*—A. Michael Chambers
(74) *Attorney, Agent, or Firm*—Yonggang Ji

(57) ABSTRACT

A uniform fluid distribution system (2) for use with a liquid transfer system (100) for maintaining an interface between liquid phases within a large scale separator system including a cell of circular or rectilinear cross-section into which liquid may be introduced as discrete phases at an inlet zone occupying a first approximately transverse cross-sectional region of said cell and output at an outlet zone occupying a second approximately transverse cross-sectional region of said cell. Said distribution system (2) comprises at least one liquid inlet (24) and one distribution outlet (32), which are connected by an internal flow connection system (36). Wherein said distribution outlet (32) is an annular or rectilinear distribution-slot (32) with a radius or distance r to the midpoint between an inner slot-radius or distance from the cell center and an outer slot-radius or distance from the cell center, said radii or distances from the cell center defining a slot-width w, through which annular or rectilinear distribution-slot (32) liquid entering said inlet is distributed to said cell along an approximately horizontal plane, and said internal flow connection system (36) is formed such that it provides an essentially uniform fluid flow through the distribution-slot (32).

13 Claims, 6 Drawing Sheets

SCALABLE INLET LIQUID DISTRIBUTION SYSTEM FOR LARGE SCALE CHROMATOGRAPHY COLUMNS

CROSS REFERENCE TO RELATED APPLICATIONS

This application is a filing under 35 U.S.C. § 371 and claims priority to international patent application number PCT/EP02/05144 filed May 10, 2002, published on Nov. 21, 2002 as WO02/093159, and to foreign application number 0111486.7 filed in Great Britain on May 11, 2001, the entire disclosures of which are hereby incorporated by reference.

FIELD OF THE INVENTION

The present invention relates to a liquid distribution system for chromatography columns. More specifically, the invention relates to a scalable liquid distribution system for large-scale chromatography columns.

BACKGROUND OF THE INVENTION

In separation procedures, particularly in liquid chromatography, the fluid distribution system is critical to the overall performance, and becomes more so as the cross-section of the chromatographic column increases.

Columns used in liquid chromatography typically comprise a body-forming structure enclosing a porous media through which a carrier liquid flows, with separation taking place by material distribution between the carrier liquid and solid phase of the porous media Typically, the porous media is enclosed in the column as a packed bed, typically formed by consolidating a suspension of discrete particles. An alternative to the packed bed is the so-called expanded or fluidised bed, where effective porosity and volume of the expanded bed depends on the fluid velocity. The term 'packing' shall be used in the following to describe the porous solid phase in all types of chromatography. The efficiency of the chromatographic separation relies in both modes strongly on the liquid distribution and collection system at the fluid inlet and outlet of the packing.

Ideally, the carrier liquid is uniformly introduced throughout the surface at the top of the packing, flows through the packing at the same velocity throughout the packing cross section, and is uniformly removed at the plane defined by the bottom of the packing.

Conventional distribution systems for use in liquid chromatography must address a number of inherent problems that have deleterious effects on the separation efficiency of the column. Among these problems are (a) non-uniform initial fluid distribution at the top of the packing as well as non-uniform fluid collection at the outlet of the packing and (b) "channelling", which is described by a non-uniform flow field within a packing, typically caused by pressure gradients that are perpendicular to the mean direction of velocity due to pressure loss in the fluid distribution system.

With respect to the channelling problem, conventional distribution systems often rely upon the pressure drop in the distributor of a vertical chromatographic column to distribute the fluid uniformly horizontally. Whenever the pressure drop through the column is high relative to the pressure drop in the distributor, however, the fluid tends to channel in the centre of the column causing excessive dispersion. This severely limits the effectiveness of chromatographic separations and is particularly acute for large diameter columns.

The problem of non-uniform initial fluid distribution refers generally to the problem of applying a sample volume simultaneously over the cross-sectional area of the packing. Without a simultaneous introduction of fluid in the plane defined by the top of the packing, it is virtually impossible to achieve uniform flow distribution through the packing.

Both problems will lead to increased dispersion in the chromatographic system by broadening the convective residence time distribution of a tracer substance transported with the fluid throughout the system. The dispersion generated by the liquid distribution system has to be controlled in relation to the amount of dispersion introduced by the chromatographic packing itself by means of diffusion and mixing effects.

Standard fluid distribution systems consist of one central inlet for the mobile phase in combination with a thin distribution channel (gap) behind the filter (woven net or sinter) confining the top and bottom plane of the inlet and outlet of the packing. In theory and from experience it is known that such a system deteriorates in performance with increasing diameter of the column. This is due to the residence time difference between fluid elements traveling from the inlet to the outer column wall and those fluid elements which directly can enter the net and the packed bed region below the inlet port. This difference in residence time is enlarged with column diameter and leads to chromatographic band broadening which becomes most severe with small particles. This problem corresponds to the non-uniform initial fluid distribution.

Columns with multiple inlets have been proposed. Multiple inlets reduce the residence time differences but are expensive to produce.

Another well-known technique for distribution is the plate system, typically utilising a plate with face openings along radii on the plate to achieve fluid distribution by decreasing the resistance of fluid flow through the plate with increasing radius. A drawback of the plate system is that the spacing and size of the openings in the plate must be calculated for any particular fluid according to its viscosity and other physical characteristics (the rheology of the fluid) so that the system will work properly with that particular fluid at a particular flow rate. A drawback to the plate system, however, is that variations in the fluid being distributed or the flow rate will affect the uniformity of the distribution.

A third technique is disclosed in U.S. Pat. No. 4,537,217, which is comprised of a layered distribution structure, comprising a first layer that acts as a cover and in which a fluid inlet is formed, a second layer wherein a number of channels are formed which each terminates in an outlet extending through the second layer. The outlets form a well-distributed pattern, which provides a high degree of fluid distribution on the packing side of the distribution system. Although this system provides excellent distribution, it suffers from several disadvantages, especially in that it is difficult to produce especially for large diameters. There is further a risk for sanitary problems due to the troublesome cleaning of such a large amount of channels of such small size, and in that it is impossible to prevent fluid from entering in between the two layers.

As a further development of the last technique, U.S. Pat. No. 5,354,460 discloses the use of a large number of fan shaped "stepdown nozzles", similar to the layered distribution structure presented above, that are arranged in concentric rings and interconnected by a manifold system. Due to the modular construction this system may be produced using large-scale production techniques, but the high grade of complexity still results in high production costs. Like the layered distribution structure, complex systems of this type are extremely difficult to clean; whereby there is an obvious risk for sanitary problems.

Another problem is that existing techniques makes it difficult to upscale from laboratory columns (small diameter) to production columns of large diameter, as it is extremely difficult to forecast the distribution characteristics. Whereby large-scale experiments have to be done to adapt laboratory processes for large-scale production to achieve an optimal process. Furthermore, it is difficult and expensive to alter the distribution characteristics of such systems.

Despite the high level of activity in the field of chromatography over many years, and the many distribution systems proposed, both speculative as well as experimentally evaluated, the need still exists for an effective, simple distribution system that will permit large liquid chromatographic columns to be used. Further there is need for a distribution system which is easily scaleable not only to different column sizes, but also to different individual combinations of packing geometry and properties, fluid properties and velocities and application types. To date, no distribution system is available which meets this end.

As used herein and in the appended claims: the term "fluid system" is intended to designate the apparatus in which liquid is either introduced to or withdrawn from a cell at a zone approximately transverse the direction of flow through the cell. The term "cell" is intended to include the terms "vessel" and "column", as well as any other structure utilised by practitioners of the separation arts, to effect a separation and/or extraction of components from an admixture by bringing the admixture into contact with solid or liquid exchange media, above referred to as the packing. "Cross-sectional zone" (or region) refers to a region within a cell bounded by cross sections of the cell-oriented transverse (typically approximately normal) the longitudinal direction of flow through the cell. "Longitudinal direction of flow" refers to the direction of flow from an inlet towards an outlet within a cell. "Longitudinal" is used consistently to designate the dominant flow path of fluid through a cell without regard to direction. "Flow connection system" refers to a system of channels or paths that connect two points in a fluid circuit. "Distribution system" refers to structures through which fluids are introduced to a cell and "collection system" refers to structures used to withdraw fluids from a cell, in each instance from a cross-sectional zone.

SUMMARY OF THE INVENTION

The object of the invention is to provide a liquid distribution system for a fluid system, which overcomes the drawbacks of the prior art systems. This is achieved by the liquid distribution system as defined in claim 1.

One advantage with such a liquid distribution system is that it provides excellent distribution characteristics.

Another advantage is that the proposed liquid distribution system is cheap to produce, compared with existing systems, particularly if made with a rotationally symmetric design.

Still a further advantage is that the proposed liquid distribution system reduces the risk for sanitary problems, due to the simple design comprising few interconnected elements.

Still a further advantage is that the proposed liquid distribution system is scalable by adjusting the geometry of the fluid paths.

Yet another advantage is that the proposed liquid distribution system facilitates a 'design by calculation' and therefore an a priori optimisation of its mean dimensions to achieve optimal performance and scalability.

Embodiments of the invention are defined in the dependent claims.

DETAILED DESCRIPTION OF THE INVENTION

The present invention disclose a uniform fluid distribution system for use with a liquid transfer system for maintaining an interface between liquid phases within a large scale separator system including a cell of circular cross-section. Into which cell, liquid may be introduced as discrete phases via the distribution system to an inlet zone occupying a first approximately transverse cross-sectional region of said cell whereby a discrete liquid phase plug is developed. Thereafter the discrete liquid phase plug migrates approximately longitudinally in a direction normal said first cross-sectional region towards an outlet zone occupying a second approximately transverse cross-sectional region of said cell. Generally spoken the distribution system comprises at least one liquid inlet and at least one distribution outlet, which are connected by an internal flow connection system.

As the features of the distribution system according to the present invention may be applied to a collection system at the column outlet, it should be understood that such collection systems are to be included within the scope of this application. In contrast to distributors known from prior art, the proposed design is symmetric which minimises production cost. Further, the symmetry simplifies a 'design by calculation' of the most favourable liquid distributor for a given separation task by applying numerical methods of 'computational fluid dynamics'. The mechanical simplicity also reduces the risk for sanitary problems.

Due to the symmetric design of the proposed distribution system 2, said distribution outlet becomes an essentially annular/rectilinear distribution-slot, with a radius/distance r to the midpoint between an inner slot radius/distance and an outer slot radius/distance, said radii/distance defining a slot-width w. Liquid entering said inlet is thus distributed to said cell along an approximately horizontal plane through the annular/rectilinear distribution-slot.

To achieve optimum performance the internal flow connection system is formed such that it provides an essentially uniform fluid flow through the distribution-slot, and such that essentially no broadening of the phase plug occurs.

To meet the above requirements the internal flow connection system may be essentially rotationally symmetric.

Figure 1:
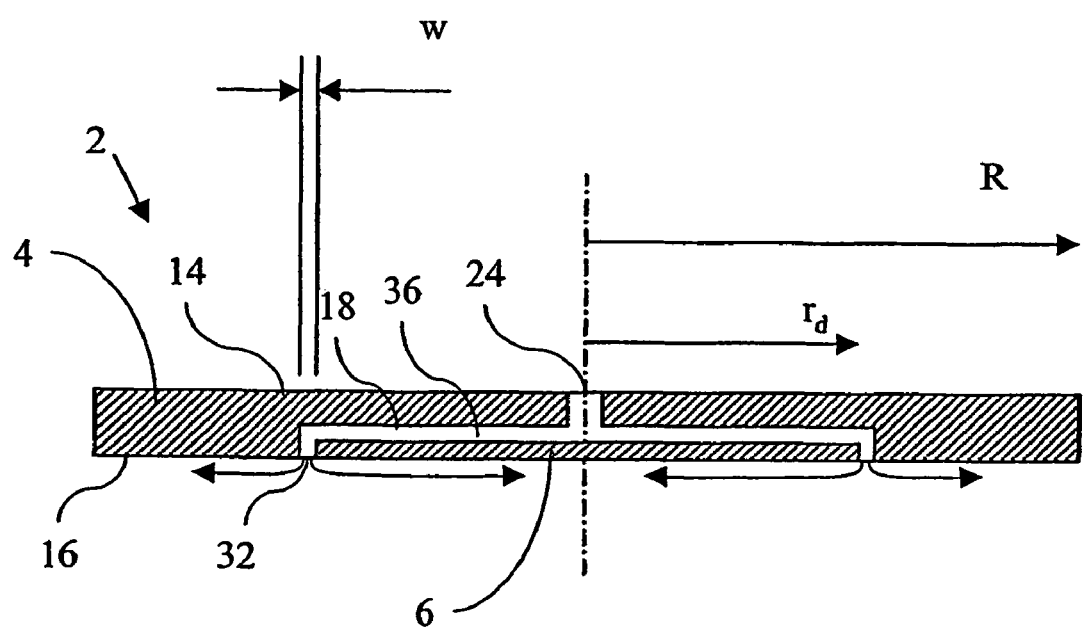
FIG. 1 is a side view of a distribution system according to the invention, in cross-section.

FIG. 1 shows an example of a distribution system 2 according to the present invention in cross-section. The distribution system 2 is essentially rotationally symmetric and is comprised of a circular main body 4, and a disc shaped distribution body 6.

The main body 4 has a top and a bottom surface 14 and 16, and a concentric circular recess 18 formed in the bottom surface 16. The main body 4 further comprises an inlet connection 24 between the sample inlet and the recess. This inlet connection 24 is preferably formed such that liquid entering through the same is distributed in an essentially rotationally symmetric manner.

The disc shaped distribution body 6 is concentrically arranged in said recess 18 and formed such that an annular distribution slot 32 is formed between the inner periphery of the recess 18 and the outer periphery of the disc shaped distribution body 6, and that a radial flow connection 36 is formed between the top of the disc shaped distribution body 6 and the bottom of the recess 18.

Figure 2:
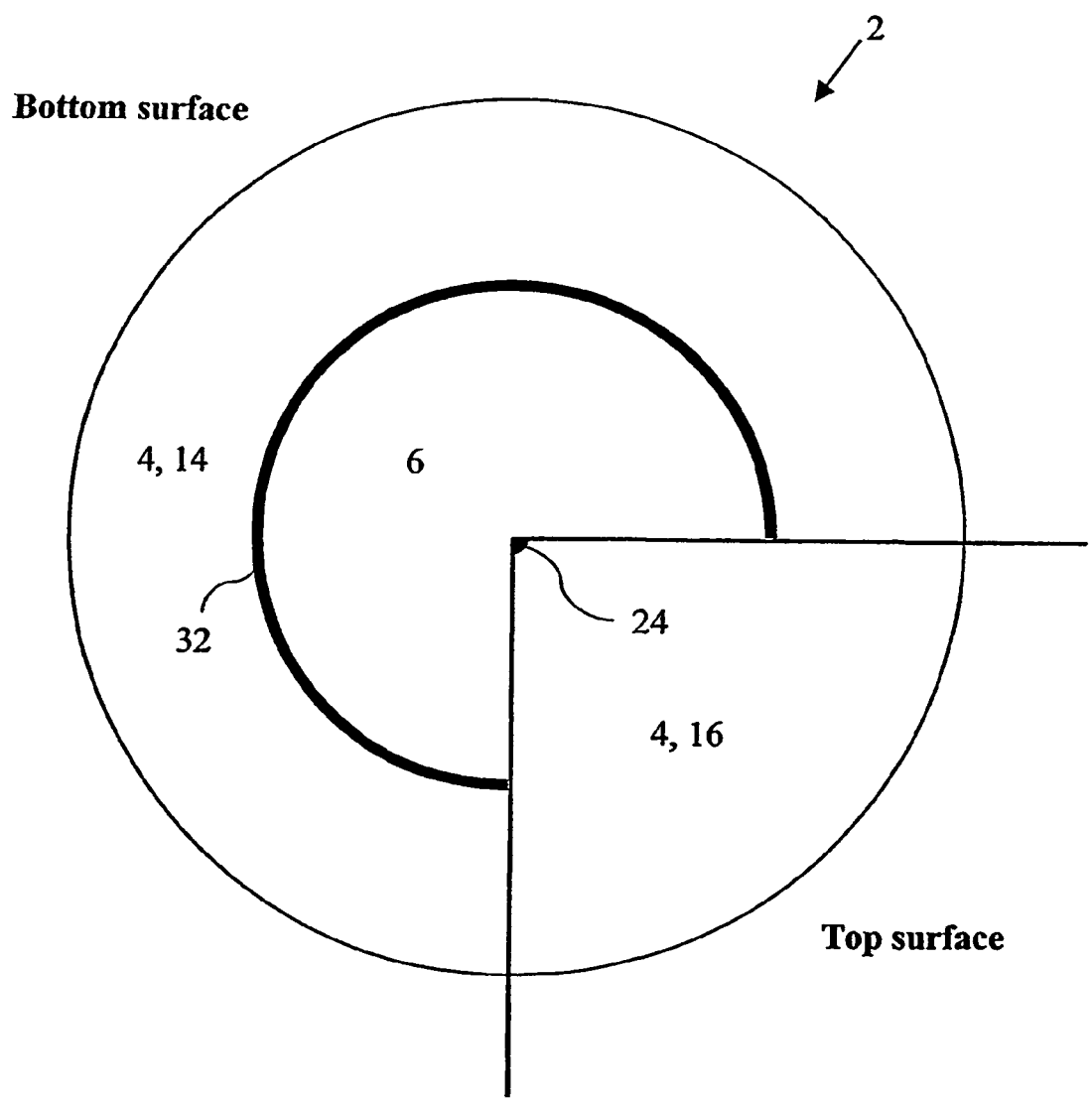
FIG. 2 shows a first embodiment of a distribution system according to the invention, seen partly from the top and partly from the bottom

In FIG. 2 the distribution system according to the inventions is shown partly from the top and partly from the bottom As is shown in FIG. 1, the annular distribution-slot 32 provides a distributed liquid flow to an associated central distribution-area A1 extending inwards from r to the centre of the cell and a peripheral distribution-area A2 extending outwards from r to the edge of the cell.

During fluid flow calculations (see below) it has surprisingly been found the radius r of the annular distribution-slot 32 should be chosen such that the central distribution-area A1 is smaller than the peripheral distribution-area A2. Preferably the radius r of the distribution-slot 32 should be chosen such that the ratio between the central distribution-area A1 to the peripheral distribution-area A2 is in the interval 37:63 to 49.9:50.1, more preferably in the interval 40:60 to 49.9:50.1, even more preferably in the interval 42:58 to 48:52 and most preferably approximately 45:55.

The distribution system 2 according to the present invention may be comprised of any suitable material, such as a metal, a polymer or the like. Preferably it is made of stainless steel or a rigid polymer that is resistant to all liquid solutions that may be entered into the system. The manufacturing of the components in the distribution system 2 may comprise moulding, machining, form pressing and the like. Each of the components in the distribution system 2 may be comprised of one solid body or an assembly of two or more sub-bodies, depending on the design of the system.

Figure 3:
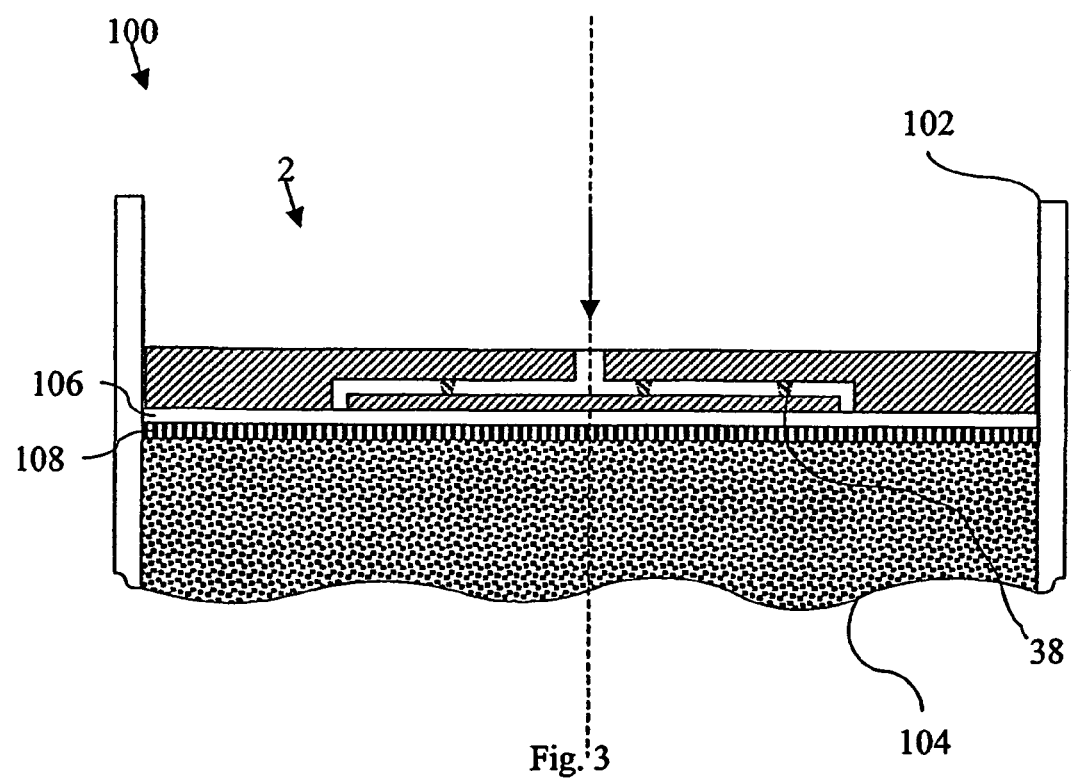
FIG. 3 is a side view in cross-section of a first embodiment of a separator system, comprising a distribution system according to the invention.

FIG. 3 is a side view of a separator system 100 in cross-section, comprising sidewalls 102, packing 104, and a distribution system 2 according to the invention. As is shown in FIG. 3, the distribution system 2 may further comprise a distribution gap 106 occupying a cross-sectional region of a predetermined height, which is located directly after the distribution slot 32 in the longitudinal direction of flow to achieve optimum distribution performance. This may be achieved by arranging a perforated plate 108 at a predetermined distance from the bottom of the main body and the distribution body, whereby at the same time the packing is prevented from entering the distribution gap 106. If a fine packing material (for example made from discrete particles) is used, the perforated plate 108 may have a fine mesh or an equivalent filter material attached on the side facing the packing 104. In one special embodiment the perforated plate 108 is comprised of a perforated plate having spacing elements that protrudes from the top surface, the spacing elements thus support the plate with respect to the bottom of the main body 4 and the distribution 6 body, thereby defining the height of said distribution gap 106.

Figure 4:
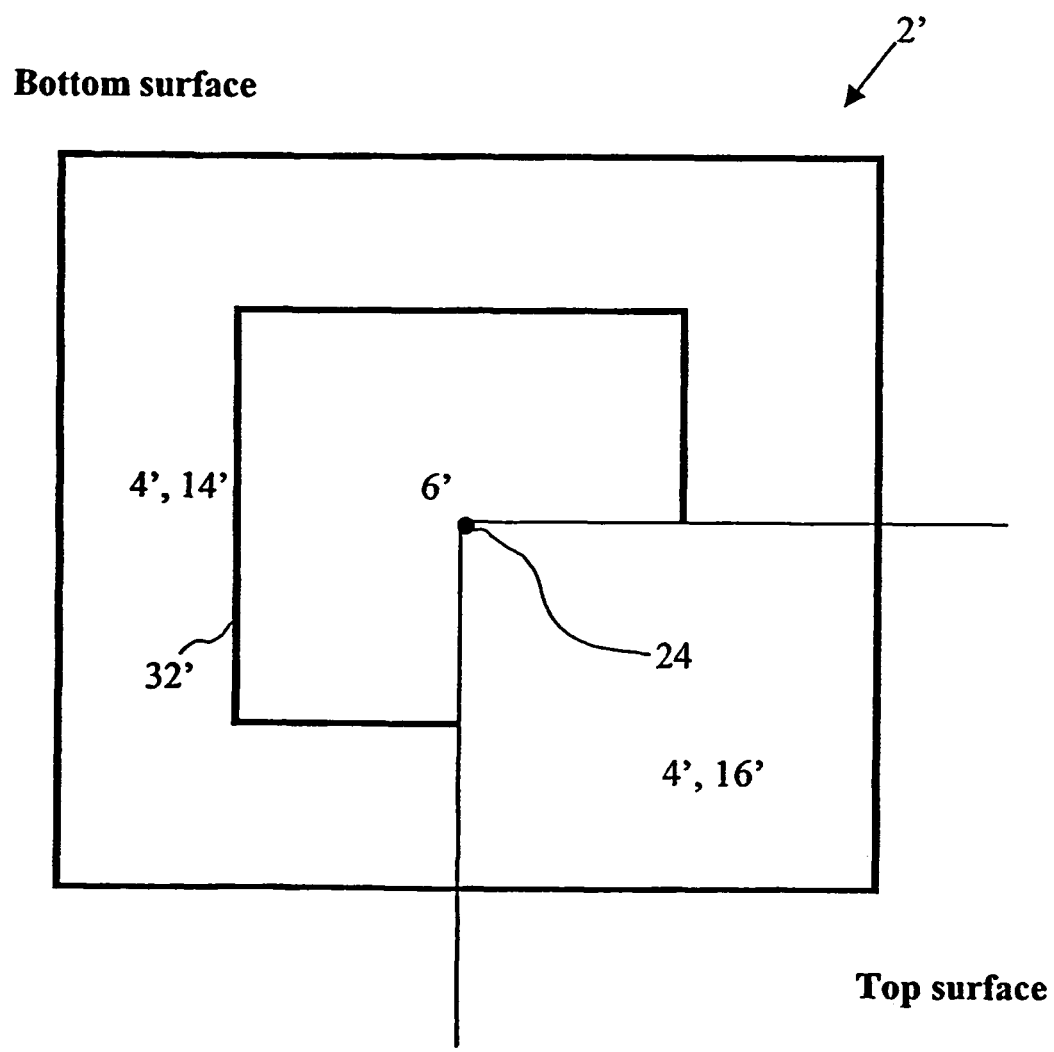
FIG. 4 shows a second embodiment of a distribution system according to the invention, seen partly from the top and partly from the bottom.

In FIG. 4 a second embodiment of a distribution system according to the invention is shown partly from the top and partly from the bottom. This embodiment differs from the first embodiment by using rectilinear, e.g. square or rectangular, plates instead of circular or annular plates. This means that the distribution slot is not circular but rectilinear. The distribution system 2' is essentially symmetric and is comprised of a square main body 4', and a rectilinear distribution body 6'.

The main body 4' has a top and a bottom surface 14' and 16', and a concentric rectilinear recess formed in the bottom surface 16'. The main body 4' further comprises an inlet connection 24' between the sample inlet and the recess. This inlet connection 24' is preferably formed such that liquid entering through the same is distributed in an essentially rotationally symmetric manner.

The rectilinear distribution body 6' is concentrically arranged in said recess and formed such that a rectilinear distribution slot 32' is formed between the inner periphery of the recess 1 and the outer periphery of the rectilinear distribution body 6', and that a radial flow connection is formed between the top of the rectilinear distribution body 6' and the bottom of the recess.

In one embodiment of the invention the radial flow connections 36 are formed by providing spacing elements 38 (shown by dotted lines in FIG. 3), such as pins, bosses, shims or the like that protrude from the top surface of the distribution body 6. In this embodiment the spacing elements support the distribution body 6 with respect to the bottom of the recess, thereby defining the height of said radial flow connection 36.

The advantage of using a flow connection 36 of constant height (for example spacing elements of constant height) lies in the simplicity of the mechanical design and low production cost.

Figure 5:
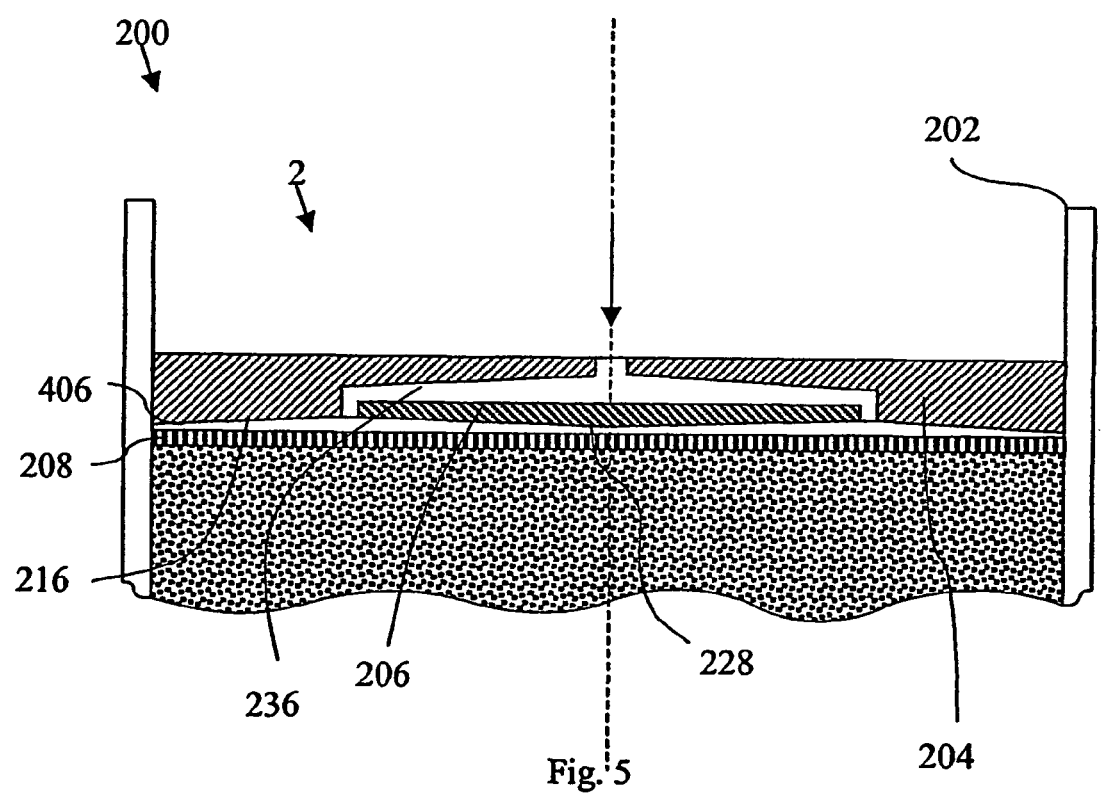
FIG. 5 is a side view in cross-section of a further embodiment of a separator system, comprising a distribution system according to the invention.

In another preferred embodiment shown in FIG. 5, the radial flow connections 236 have a conical shaped or tapered fluid path with the largest channel height at the position of highest fluid velocity to balance the volumetric flow in the path. With regard to chromatographic performance, a conical shaped radial flow connection 236 with large channel height near the position of highest fluid velocity is preferable. Such a design could be implemented easily when building the distribution system for example from cast/moulded material/plastic. The conical flow paths can be formed by making the one or more of the mutually facing surfaces 216, 228 of the main body 204 and the distribution body 206 conical or semi-conical.

The principle of conical shaped or tapered fluid paths may further be applied to the distribution gap 406, whereby it may be conically shaped with respect to the distribution slots such that the fluid path has a larger channel height at the position of higher fluid velocity.

To minimise turbulence and the like in the radial flow connections 36, edges and corners therein are preferably rounded by fillets or chamfers that are applied to the edges of the distribution bodies anywhere the fluid is changing the main direction of flow.

In one further embodiment the distribution system 2 is formed such that it may be fitted as a distribution cartridge in a cell end-piece which can be combined with a standard end piece and standard nozzle for each column diameter. A design advantage of this embodiment is the fact that all column end pieces (adapters) may be fitted with one single inlet nozzle for the mobile phase irrespective of the complexity of the internal fluid distribution system 2. A modular distribution system of this type allows replacement of the distribution system cartridge to adapt the column for a different type of media/application, whereby reduced cost and increased flexibility is achieved.

In one further embodiment the distribution system 2 is formed such that it may be fitted with one or multiple nozzles dedicated for the introduction of the packing material as a slurry into the cell. Preferably, one slurry nozzle is fitted in the centre of the cell/end piece/distribution system/filter. In such cases the liquid inlet 24 have to be arranged such that it is capable of providing a radially homogeneous flow, e.g. it may be of annular shape and surround said slurry nozzle.

Due to the simple design the distribution system 2 according to the invention is scalable with respect to the chromatographic functionality, in that it provides chromatographic performance that is adjusted to the requirements of different media/applications and column diameters.

Scalability in the design is achieved by adjusting the geometry of the fluid path in the distribution system 2.

Numerical parameter studies with a fluid dynamics code specifically developed for the distributor design revealed that the most favourable placement of the distribution slot 32 is chosen such that the ratio of the central distribution-area A1 to the peripheral distribution-area A2 is approximately 45:55. This corresponds to a placement of the distribution slot 32 with a radius $r_d$ relative to the column radius R by a ratio $r_d/R=0.67$.

Figure 6:
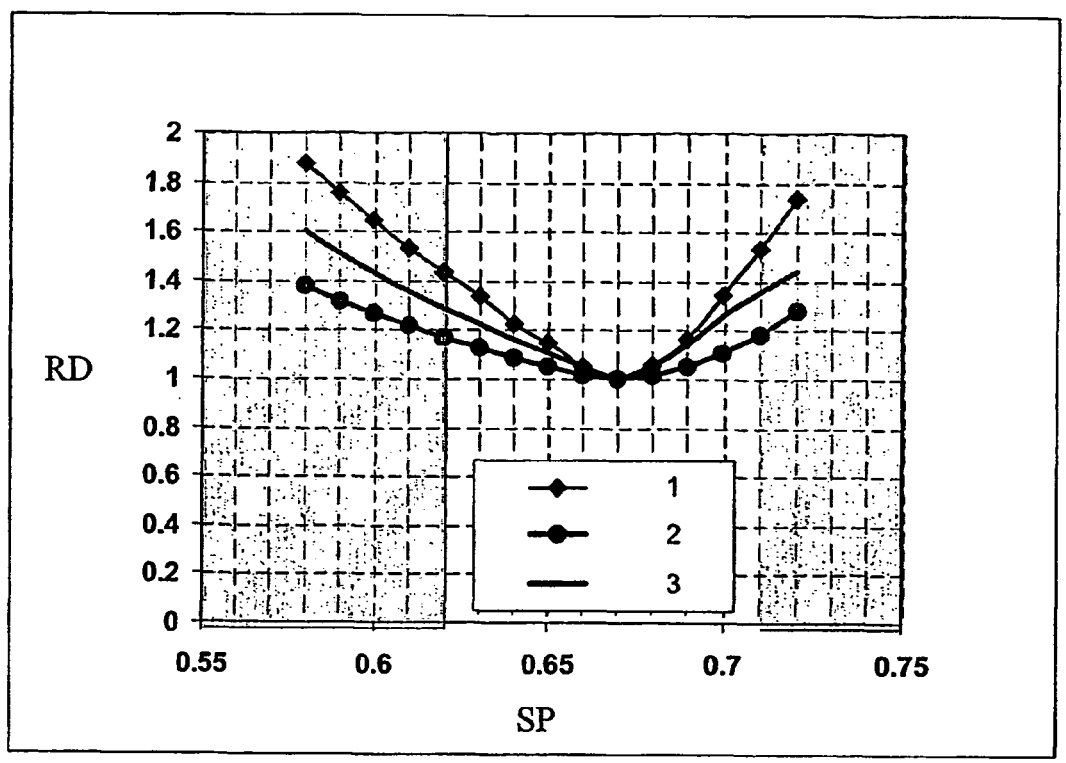
FIG. 6 is a graph showing a comparison of dispersion efficiency against slot position for 3 examples of columns in accordance with the present invention.

FIG. 6 shows a comparison of relative dispersion RD introduced by the distributor against slot position SP for 3 examples of columns in accordance with the present invention. The relative dispersion denotes the dispersion introduced by the liquid distribution system normalised to the minimum dispersion introduced by the liquid distribution system with an optimised slot position. The dispersion introduced by the liquid distribution system relative to the overall dispersion of the chromatographic unit is different in the three examples. In case 1 the column diameter is 450 mm, the distribution channel height is 1 mm, the pre-distribution channel height 2 mm, the media 180 μm mean diameter particles, the packed bed permeability 1.E-11 m$^2$ and the bed height 100 mm. In case 2 the column diameter is 450 mm, the distribution channel height is 0.4 mm, the pre-distribution channel height 0.8 mm, the media 30 μm mean diameter particles, the packed bed permeability 5.E-13 m$^2$ and the bed height 150 mm. In case 3 the column diameter is 450 mm, the distribution channel height is 0.6 mm, the predistribution channel height 1 mm, the media 90 μm mean diameter particles, the packed bed permeability 2.E-12 m$^2$ and the bed height 100 mm. All the channels are of constant height. In all three examples, the most favourable performance was achieved with a slot placement $r_d/R=0.67$ (where R is the radius of the column and $r_d$ is the radial distance from the centre of the column of the middle of the slot) which corresponds to a ratio of the central distribution-area A1 to the peripheral distribution-area A2 that is approximately 45:55.

On basis of the computations, one can show that scalability in the design of the distribution system 2 according to the invention can be achieved by designing a distribution system 2 with a dispersion appropriate for each individual combination of packing geometry and column size, packing properties, fluid properties and velocity, and specific application demands. The preferred variables for the design of the distribution system 2 is the height of the radial flow connection 36 and distribution gap, whereas the aspect ratios for the placement of the distribution slot as such can be kept constant.

While the invention has been illustrated by examples in which the distribution system comprises a continuous distribution slot 32, i.e. a slot forming a continuous circular opening it is conceivable to use a distribution slot that is not continuous. This could, for example, be formed of a plurality of holes or (curved) slots arranged in a circle, the holes being positioned and dimensioned such that they distribute fluid with substantially the same effect as a continuous distribution slot.

The various improvements shown in the embodiments may be combined, for example by using a rectilinear slot with tapered distribution channels and/or gaps.

Additionally it is possible to use column cross-section and distribution slot shapes other than circular or rectilinear, for example, triangular, pentagonal or other polygonal shapes, or shapes formed by intersecting circles.

The invention is not limited by the illustrative examples above, but is intended to encompass all embodiments covered by the following claims.

The invention claimed is:

1. A uniform fluid distribution system (2) for use with a chromatography column including a cell of circular cross-section or rectilinear cross-section into which liquid may be introduced as discrete phases at an inlet zone occupying a first approximately transverse cross-sectional region of said cell and output at an outlet zone occupying a second approximately transverse cross-sectional region of said cell, said distribution system (2) comprising at least one liquid inlet (24) and one distribution outlet (32:32'), which are connected by an internal flow connection system (36), wherein, said distribution outlet (32) consists of an annular or rectilinear distribution-slot (32:32') with a radius or distance to the midpoint r between an inner slot-radius or distance from the cell centre and an outer slot-radius or distance from the cell centre, said radii or distances from the cell centre defining a slot-width w, through which annular distribution-slot (32) or rectilinear slot (32') liquid entering said inlet is distributed to said cell along an approximately horizontal plane, wherein the distribution-slot (32: 32') is arranged between an associated central distribution-area (A1) extending inwards from r to the centre of the cell, and a peripheral distribution-area (A2) extending outwards from r to the edge of the cell, and the radius or distance r of the distribution-slot (32:32') from the centre of the cell is such that the central distribution-area (A1) is smaller than the peripheral distribution-area (A2).

2. The distribution system (2) of claim 1, wherein the radius r or distance from the centre of the distribution-slot (32:32') is chosen such that the ratio between the central distribution-area (A1) to the peripheral distribution-area (A2) is in the interval 37:63 to 49.9 to 50.1.

3. The distribution system (2) of claim 1, wherein the radius r of the annular distribution-slot (32) or distance from the centre of the rectilinear distribution slot (32') is chosen such that the ratio between the central distribution-area (A1) to the peripheral distribution-area (A2) is in the interval 40:60 to 49.9:50.1.

4. The distribution system (2) of claim 1, wherein the radius r of the annular distribution-slot (32) or distance from the centre of the rectilinear distribution slot (32') is chosen such that the ratio between the central distribution-area (A1) to the peripheral distribution-area (A2) is approximately 45:55.

5. The distribution system (2) of claim 1, wherein the internal flow connection system (36) is essentially rotationally symmetric.

6. The distribution system (2) of claim 1, which includes a circular main body (4) having a top and a bottom surface (14, 16), said main body (4) having a circular recess (18) formed in the bottom surface (16), and an inlet liquid connection between the liquid inlet (24) and the recess (18), and a disc-shaped distribution body (6) concentrically arranged in said recess (18) and formed such that an annular distribution slot (32) is formed between the inner periphery of the recess (18) and the outer periphery of the distribution body (6), and such that a radial flow connection (36) is created between the top of the distribution body (6) and the bottom of the recess (18).

7. The distribution system (2) of claim 6, wherein said disc-shaped distribution body (6) includes a plate having spacing elements that protrude from the top surface, the spacing elements support the distribution body (6) with respect to the bottom of the recess (18), thereby defining the height of said radial flow connection (36).

8. The distribution system (2) of claim 1, wherein the internal flow connection system (36) has a conical shaped or tapered fluid path with large channel height at the position of highest fluid velocity.

9. The distribution system (2) of claim 1, including a distribution gap (106) occupying a cross-sectional region of a predetermined height, located directly after the distribution slot (32) in the longitudinal direction of flow.

10. The distribution system (2) of claim 9, wherein the distribution gap (206) is conically shaped or tapered with respect to the distribution slot, and is formed such that the fluid path has a larger channel height at the position of higher fluid velocity.

11. The distribution system (2) of claim 1, including a perforated plate (108) terminating the distribution gap (106) in the longitudinal direction of flow.

12. The distribution system (2) of claim 11, wherein the perforated plate (108) is comprised of a perforated plate having spacing elements that protrude from the top surface, the spacing elements support the plate with respect to the bottom of the main body (4) and the distribution body (6), thereby defining the height of said distribution gap (106).

13. The distribution system (2) of claim 1, wherein the flow connection system (36) comprises fillets/chamfers applied to the edges of the distribution body (6) anywhere the fluid is changing the main direction of flow.

* * * * *